US010898249B2

(12) United States Patent
Palmer et al.

(10) Patent No.: US 10,898,249 B2
(45) Date of Patent: Jan. 26, 2021

(54) SELF-COMPRESSING SCREWS FOR GENERATING AND APPLYING COMPRESSION WITHIN A BODY

(71) Applicant: MX Orthopedics, Corp., Lexington, MA (US)

(72) Inventors: Matthew Palmer, Cambridge, MA (US); Kaitlyn Nealon, Boston, MA (US); Robert Devaney, Auburndale, MA (US); Matthew Fonte, Concord, MA (US)

(73) Assignee: Arthrex, Inc., Naples, FL (US)

( * ) Notice: Subject to any disclaimer, the term of this patent is extended or adjusted under 35 U.S.C. 154(b) by 0 days.

(21) Appl. No.: 15/009,521

(22) Filed: Jan. 28, 2016

(65) Prior Publication Data

US 2016/0213412 A1    Jul. 28, 2016

Related U.S. Application Data

(60) Provisional application No. 62/108,843, filed on Jan. 28, 2015.

(51) Int. Cl.
*A61B 17/86* (2006.01)
*A61B 17/70* (2006.01)

(52) U.S. Cl.
CPC .......... *A61B 17/863* (2013.01); *A61B 17/866* (2013.01); *A61B 17/7037* (2013.01); *A61B 17/864* (2013.01)

(58) Field of Classification Search
CPC .................... A61B 17/863; A61B 17/866
See application file for complete search history.

(56) References Cited

U.S. PATENT DOCUMENTS 2,580,821 A    1/1952    Nicola
3,960,147 A    6/1976    Murray
(Continued)

FOREIGN PATENT DOCUMENTS

CA    2391115    12/2002
EP    0826340 A2    3/2008
(Continued)

OTHER PUBLICATIONS

International Preliminary Report on Patentability for PCT Application No. PCT/US2016/015432 dated Aug. 10, 2017.
(Continued)

*Primary Examiner* — Olivia C Chang
(74) *Attorney, Agent, or Firm* — Carlson, Gaskey & Olds, P.C.

(57) ABSTRACT

A compression screw comprising: a shaft capable of being stretched, the shaft having a proximal end and a distal end, the proximal end of the shaft comprising a bone-engaging feature and the distal end of the shaft comprising a distal screw thread, and the proximal end of the shaft comprising a drive feature for turning the shaft; wherein inserting the compression screw into bone across a fracture line generates a force, and wherein the force generates a stress in the shaft that causes the shaft to stretch to less than its elastic limit; and wherein, after the shaft is inserted into a bone, the shaft attempts to foreshorten to its original un-stretched condition, thereby generating and maintaining compression across the fracture line.

22 Claims, 15 Drawing Sheets

(56) References Cited

U.S. PATENT DOCUMENTS

| | | |
|---|---|---|
| 4,175,555 A | 11/1979 | Herbert |
| 4,428,376 A | 1/1984 | Mericle |
| 4,444,181 A | 4/1984 | Wevers et al. |
| 4,503,569 A | 3/1985 | Dotter |
| 4,512,338 A | 4/1985 | Balko et al. |
| 4,570,623 A | 2/1986 | Ellison et al. |
| 4,733,665 A | 3/1988 | Palmaz |
| 4,858,601 A | 8/1989 | Glisson |
| 4,905,679 A | 3/1990 | Morgan |
| 4,922,905 A | 5/1990 | Strecker |
| 4,950,227 A | 8/1990 | Savin et al. |
| 4,959,064 A | 9/1990 | Engelhardt |
| 4,959,065 A | 9/1990 | Arnett et al. |
| 5,026,390 A | 6/1991 | Brown |
| 5,044,540 A | 9/1991 | Dulebohn |
| 5,061,275 A | 10/1991 | Wallsten et al. |
| 5,089,006 A | 2/1992 | Stiles |
| 5,098,434 A | 3/1992 | Serbousek |
| 5,246,443 A | 9/1993 | Mai |
| 5,474,557 A | 12/1995 | Mai |
| 5,607,530 A | 3/1997 | Hall et al. |
| 5,680,981 A | 10/1997 | Mililli et al. |
| 5,766,218 A | 6/1998 | Arnott |
| 5,779,707 A | 7/1998 | Bertholet et al. |
| 5,876,434 A | 3/1999 | Flomenblit et al. |
| 5,947,999 A | 9/1999 | Groiso |
| 6,030,162 A | 2/2000 | Huebner |
| 6,048,344 A | 4/2000 | Schenk |
| 6,187,009 B1 | 2/2001 | Herzog et al. |
| 6,306,140 B1 | 10/2001 | Siddiqui |
| 6,325,805 B1 | 12/2001 | Ogilvie et al. |
| 6,533,157 B1 | 3/2003 | Whitman |
| 6,569,173 B1 | 5/2003 | Blatter et al. |
| 6,607,530 B1 | 8/2003 | Carl et al. |
| 6,623,486 B1 | 9/2003 | Weaver et al. |
| 6,656,184 B1 | 12/2003 | White et al. |
| 6,685,708 B2 | 2/2004 | Monassevitch et al. |
| 6,761,731 B2 | 7/2004 | Majercak |
| 6,773,437 B2 | 8/2004 | Ogilvie et al. |
| 7,175,626 B2 | 2/2007 | Neff |
| 7,229,452 B2 | 6/2007 | Kayan |
| 7,481,832 B1 | 1/2009 | Meridew et al. |
| 7,582,107 B2 | 9/2009 | Trail et al. |
| 7,618,441 B2 | 11/2009 | Groiso |
| 7,625,395 B2 | 12/2009 | Muckier |
| 7,794,483 B2 | 9/2010 | Capanni |
| 7,875,070 B2 | 1/2011 | Molaei |
| 7,955,388 B2 | 6/2011 | Jensen et al. |
| 7,976,648 B1 | 7/2011 | Boylan et al. |
| 7,985,222 B2 | 7/2011 | Gall et al. |
| 7,993,380 B2 | 8/2011 | Hawkes |
| 8,048,134 B2 | 11/2011 | Partin |
| 8,080,044 B2 | 12/2011 | Biedermann et al. |
| 8,114,141 B2 | 2/2012 | Appenzeller et al. |
| 8,118,952 B2 | 2/2012 | Gall et al. |
| 8,137,351 B2 | 3/2012 | Prandi |
| 8,216,398 B2 | 7/2012 | Bledsoe et al. |
| 8,221,478 B2 | 7/2012 | Patterson et al. |
| 8,393,517 B2 | 3/2013 | Milo |
| 8,425,588 B2 | 4/2013 | Molaei |
| 8,486,121 B2 | 7/2013 | Biedermann et al. |
| 8,584,853 B2 | 11/2013 | Knight et al. |
| 8,597,337 B2 | 12/2013 | Champagne |
| 8,721,646 B2 | 5/2014 | Fox |
| 8,790,379 B2 | 7/2014 | Bottlang et al. |
| 8,801,732 B2 | 8/2014 | Harris et al. |
| 8,808,294 B2 | 8/2014 | Fox et al. |
| 8,864,804 B2 | 10/2014 | Champagne et al. |
| 9,017,331 B2 | 4/2015 | Fox |
| 9,095,338 B2 | 8/2015 | Taylor et al. |
| 9,101,349 B2 | 8/2015 | Knight et al. |
| 9,204,932 B2 | 12/2015 | Knight et al. |
| 9,326,804 B2 | 5/2016 | Biedermann et al. |
| 9,339,268 B2 | 5/2016 | Fox |
| 9,408,647 B2 | 8/2016 | Cheney |
| 9,451,955 B2 | 9/2016 | Fox |
| 9,451,957 B2 | 9/2016 | Fox |
| 2002/0058940 A1 | 5/2002 | Frigg et al. |
| 2002/0111641 A1 | 8/2002 | Peterson et al. |
| 2002/0198527 A1 | 12/2002 | Muckter |
| 2004/0111089 A1 | 6/2004 | Stevens et al. |
| 2004/0230193 A1 | 11/2004 | Cheung et al. |
| 2004/0260377 A1 | 12/2004 | Flomenblit et al. |
| 2005/0043757 A1 | 2/2005 | Arad et al. |
| 2005/0096660 A1 | 5/2005 | Allen |
| 2005/0152770 A1 | 7/2005 | Tschakaloff et al. |
| 2005/0240190 A1* | 10/2005 | Gall .............. A61B 17/7225 606/286 |
| 2005/0277940 A1* | 12/2005 | Neff .............. A61B 17/7225 606/916 |
| 2005/0288707 A1 | 12/2005 | De Canniere et al. |
| 2006/0264954 A1* | 11/2006 | Sweeney, II ....... A61B 17/8685 606/312 |
| 2007/0233124 A1* | 10/2007 | Corrao ............... A61B 17/863 606/327 |
| 2007/0260248 A1 | 11/2007 | Tipirneni |
| 2007/0265631 A1 | 11/2007 | Fox |
| 2007/0270855 A1 | 11/2007 | Partin |
| 2008/0065154 A1 | 3/2008 | Allard et al. |
| 2008/0071373 A1 | 3/2008 | Molz et al. |
| 2008/0132894 A1 | 6/2008 | Coilard-Lavirotte et al. |
| 2008/0234763 A1 | 9/2008 | Patterson et al. |
| 2008/0249574 A1 | 10/2008 | McCombs et al. |
| 2009/0018556 A1 | 1/2009 | Prandi |
| 2009/0105768 A1 | 4/2009 | Cragg et al. |
| 2009/0198287 A1 | 8/2009 | Chiu |
| 2009/0254090 A1 | 10/2009 | Lizee |
| 2009/0264937 A1 | 10/2009 | Parrott |
| 2010/0036430 A1 | 2/2010 | Hartdegen et al. |
| 2010/0063506 A1 | 3/2010 | Fox et al. |
| 2010/0087822 A1 | 4/2010 | Groiso |
| 2010/0131014 A1 | 5/2010 | Peyrot et al. |
| 2010/0211115 A1* | 8/2010 | Tyber ............... A61B 17/863 606/305 |
| 2010/0237128 A1 | 9/2010 | Miller et al. |
| 2011/0008643 A1 | 1/2011 | Shaw et al. |
| 2011/0060372 A1 | 3/2011 | Allison |
| 2011/0144694 A1 | 6/2011 | Laeng et al. |
| 2011/0144703 A1 | 6/2011 | Krause et al. |
| 2011/0224725 A1 | 9/2011 | De Canniere et al. |
| 2011/0247731 A1 | 10/2011 | Gordon |
| 2011/0313473 A1 | 12/2011 | Prandi et al. |
| 2012/0116465 A1 | 5/2012 | Elahinia et al. |
| 2013/0030437 A1 | 1/2013 | Fox |
| 2013/0066435 A1 | 3/2013 | Averous et al. |
| 2013/0123785 A1 | 5/2013 | Fonte |
| 2013/0206815 A1 | 8/2013 | Fox |
| 2013/0231667 A1 | 9/2013 | Taylor et al. |
| 2013/0300437 A1 | 11/2013 | Grosjean et al. |
| 2014/0014553 A1 | 1/2014 | Knight et al. |
| 2014/0018809 A1 | 1/2014 | Allen |
| 2014/0020333 A1 | 1/2014 | Knight et al. |
| 2014/0024002 A1 | 1/2014 | Knight et al. |
| 2014/0097228 A1 | 4/2014 | Taylor et al. |
| 2014/0257420 A1 | 9/2014 | Fox |
| 2014/0277516 A1 | 9/2014 | Miller et al. |
| 2014/0324048 A1 | 10/2014 | Fox |
| 2014/0358187 A1 | 12/2014 | Taber et al. |
| 2014/0358247 A1 | 12/2014 | Fox et al. |
| 2015/0238237 A1 | 8/2015 | Madjarov |
| 2015/0238238 A1 | 8/2015 | Cheney |
| 2016/0051284 A1 | 2/2016 | Cronen |
| 2016/0089190 A1 | 3/2016 | Taber |
| 2016/0095638 A1 | 4/2016 | Reimels |
| 2016/0135808 A1 | 5/2016 | Anderson |
| 2016/0199060 A1 | 7/2016 | Morgan et al. |
| 2016/0235460 A1 | 8/2016 | Wahl |

(56) References Cited

U.S. PATENT DOCUMENTS

2017/0000482 A1 1/2017 Averous et al.
2017/0231625 A1 8/2017 Handie

FOREIGN PATENT DOCUMENTS

| EP | 2085039 | | 8/2009 |
|---|---|---|---|
| FR | 2787313 | A1 | 6/2000 |
| FR | 2874166 | A1 | 2/2006 |
| FR | 2901119 | A1 | 11/2007 |
| IL | 64726 | A | 2/1985 |
| JP | H0910224 | | 1/1997 |
| WO | 2009/091770 | A1 | 7/2009 |
| WO | 2014087111 | A1 | 6/2014 |

OTHER PUBLICATIONS

Cai, S. et al., Texture evolution during nitinol martensite detwinning and phase transformation, Applied Physics Letters 103, 241909 (2013).
Gruszka, Dominik et al., The Durability of the Intrascaphoid Compression of Headless Compression Screws: In Vitro Study, The Journal of Hand Surgery, Jun. 2012, pp. 1142-1150.
Huang et al., Ion release from NiTi orthodontic wires in artificial saliva with various acidities, Biomaterials, 24, 2003, pp. 3585-3592.
Supplementary European Search Report for EP Application 14861059.5 dated Sep. 6, 2017.
U.S. Appl. No. 15/079,770, filed Mar. 24, 2016, entitled "Staples for Generating and Applying Compression Within a Body".
Restriction Requirement for U.S. Appl. No. 14/699,837 dated Sep. 13, 2017.
U.S. Appl. No. 15/684,183, filed Aug. 23, 2017, entitled "Staples for Generating and Applying Compression Within a Body".
U.S. Appl. No. 15/650,210, filed Jul. 14, 2017, entitled "Staples for Generating and Applying Compression Within a Body".
U.S. Appl. No. 15/651,530, filed Jul. 17, 2017, entitled "Staples for Generating and Applying Compression Within a Body".
International Preliminary Report on Patentability for PCT Application No. PCT/US2014/065406 dated May 17, 2016.
International Preliminary Report on Patentability for PCT Application No. PCT/US2014/065553 dated May 17, 2016.
International Preliminary Report on Patentability for PCT Application No. PCT/US2015/020598 dated Sep. 13, 2016.
International Preliminary Report on Patentability for PCT Application No. PCT/US2015/028328 dated Nov. 1, 2016.
International Search Report and Written Opinion for PCT Application No. PCT/US2014/065406 dated Feb. 24, 2015.
International Search Report and Written Opinion for PCT Application No. PCT/US2014/065553 dated Feb. 24, 2015.
International Search Report and Written Opinion for PCT Application No. PCT/US2015/020598 dated Jun. 12, 2015.
International Search Report and Written Opinion for PCT Application No. PCT/US2015/028328 dated Aug. 4, 2015.
International Search Report and Written Opinion for PCT Application No. PCT/US2016/015432 dated Apr. 21, 2016.
International Search Report and Written Opinion for PCT Application No. PCT/US2016/023980 dated Jul. 21, 2016.
Non-Final Office Action for U.S. Appl. No. 14/539,650 dated Apr. 18, 2017.
Non-Final Office Action for U.S. Appl. No. 14/540,351 dated Apr. 19, 2017.
Non-Final Office Action for U.S. Appl. No. 15/650,210 dated Oct. 4, 2017.
Non-Final Office Action for U.S. Appl. No. 15/684,183 dated Oct. 10, 2017.
Supplementary European Search Report for EP Application 14862438.0 dated Jun. 12, 2017.
Supplementary European Search Report for EP Application No. 14861238.5 dated Jun. 12, 2017.
U.S. Appl. No. 14/699,837, filed Apr. 29, 2015, entitled "Controlling the Unloading Stress of Nitinol Devices and/or Other Shape Memory Material Devices".
U.S. Appl. No. 14/539,650, filed Nov. 12, 2014, entitled "Screws for Generating and Applying Compression Within a Body".
U.S. Appl. No. 14/540,351, filed Nov. 13, 2014, entitled "Staples for Generating and Applying Compression Within a Body".
European Search Report for European Patent Application No. 16744132.8 dated Oct. 24, 2018.

* cited by examiner

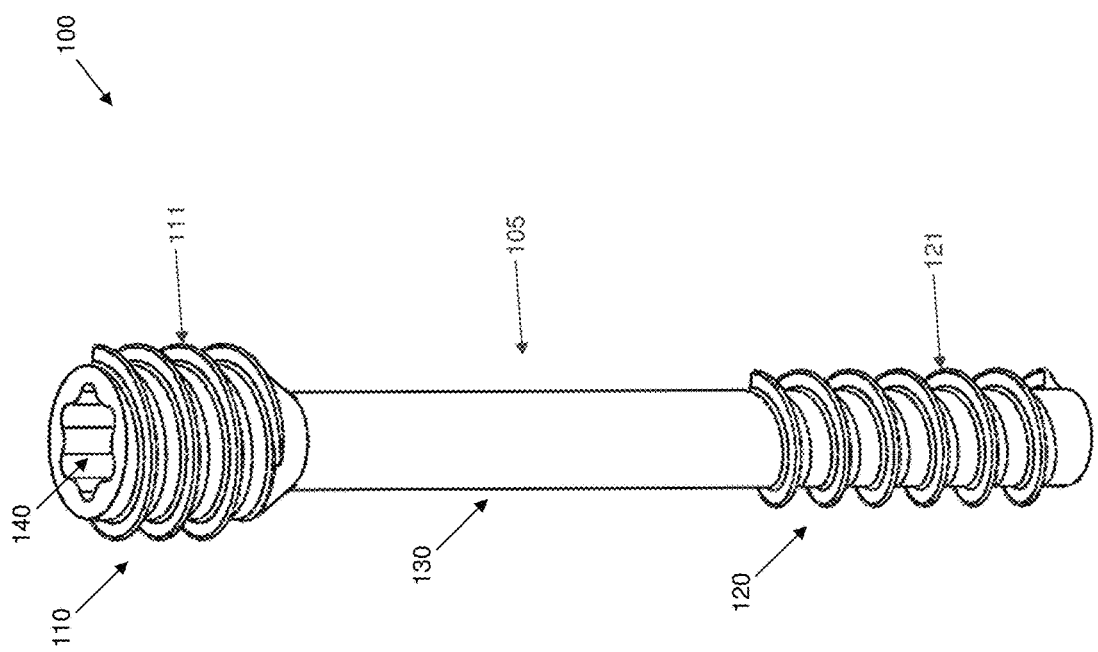

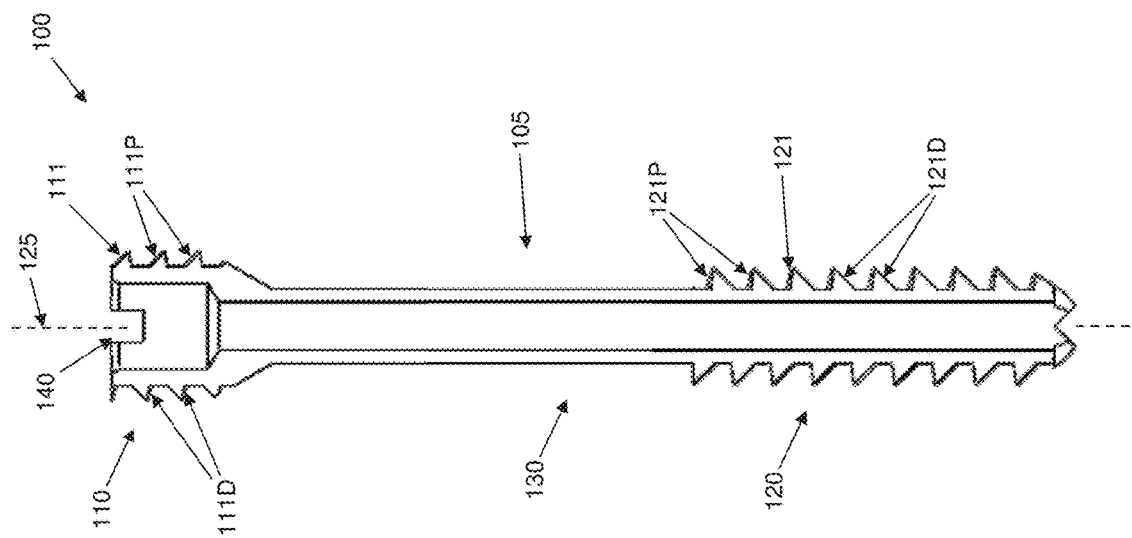

FIG. 3

| Screw Properties | |
|---|---|
| Shaft ID | 1.3 mm |
| Shaft OD | 1.9 mm |
| Cross Sectional Area | 1.51 mm$^2$ |
| Total Screw Length | 30.00 mm |
| Central Bridge Length | 10.50 mm |
| Proximal | |
| Major Diameter | 4.30 mm |
| Depth | 1.20 mm |
| Minor Diameter | 1.90 mm |
| Length | 4.50 mm |
| Pitch | 1.10 mm |
| Distal | |
| Major Diameter | 3.15 mm |
| Depth | 0.63 mm |
| Minor Diameter | 1.90 mm |
| Length | 15.00 mm |
| Pitch | 1.25 mm |

FIG. 9

To Stretch Central Bride:              Stress$_{Bridge}$ >UPS

Upper Plateau Stress                          400 MPa
Bridge Cross-Sectional Area                   1.51 mm$^2$
Force Required to Stretch Bridge              603.2 N

To Stretch Screw need                     603.2 N
of compressive load generated by thread differential

Screw Torque                                  750 Nmm
Proximal Axial Tension                        1744.2 N
Proximal Axial Stress                         32.8 MPa
Distal Axial Tension                          2381.0 N
Proximal Distal Stress                        18.3 MPa
Delta Axial Tension                           636.8 > 603.2
Axial Stress                                  422.3 MPa

FIG. 10

Proximal Thread Shear Stress

| | |
|---|---|
| Pitch | 1.10 mm |
| Nominal Radius | 2.15 mm |
| Torque | 750 Nmm |
| Torque at Radius | 348.8 N |
| Thread Circumference | 13.5 mm |
| Ratio | 13.5mm:1.1mm |
| Shear Force | 4284.0 N |
| Thread Root | 1.20 mm |
| Helix Length | 55.3 mm |
| Thread Area | 66.3 mm$^2$ |
| Shrear Stress | 64.6 MPa | > 65MPa (Shear Stress of Cortical Bone) |

Distal Thread Shear Stress

| | |
|---|---|
| Pitch | 1.25 mm |
| Nominal Radius | 1.575 mm |
| Torque | 750 Nmm |
| Torque at Radius | 476.2 N |
| Thread Circumference | 9.9 mm |
| Ratio | 9.4mm:1.25mm |
| Shear Force | 3769.9 N |
| Thread Root | 0.63 mm |
| Helix Length | 118.8 mm |
| Thread Area | 74.2 mm$^2$ |
| Shrear Stress | 50.8 MPa | > 65MPa (Shear Stress of Cortical Bone) |

FIG. 11

SELF-COMPRESSING SCREWS FOR GENERATING AND APPLYING COMPRESSION WITHIN A BODY

REFERENCE TO PENDING PRIOR PATENT APPLICATIONS

This patent application claims benefit of prior U.S. Provisional Patent Application Ser. No. 62/108,843, filed Jan. 28, 2015 by MX Orthopedics, Corp. and Matthew Palmer et al. for SELF-STRETCHING SCREWS FOR GENERATING AND APPLYING COMPRESSION WITHIN A BODY, which patent application is hereby incorporated herein by reference.

FIELD OF THE INVENTION

The present invention relates to screws for generating, applying and maintaining compression to a site in a human or animal body in order to effect healing of diseased or damaged tissue. The invention finds particular utility in the field of orthopedics and specifically for generating and maintaining compression between bone fragments. While the invention has application throughout the body, its utility will be illustrated herein in the context of the repair of injured bone tissue, such as the scaphoid of the wrist, the diaphysis of the fifth metatarsal, the proximal interphalangeal joint of the second, third, fourth, or fifth toe, the pelvis and the femoral head.

BACKGROUND OF THE INVENTION

In the field of orthopedic surgery, it is common to rejoin broken bones. The success of the bone rejoinder procedure often depends on the successful re-approximation of the bone fragments and on the amount of compression achieved between the bone fragments. If the surgeon is unable to bring the bone fragments into close proximity, a gap will exist between the bone fragments and the bone tissue will need to fill that gap before complete healing can take place. Furthermore, gaps between bone fragments that are too large allow motion to occur between the bone fragments, disrupting the healing tissue and thus slowing the healing process. Optimal healing requires that bone fragments be in close contact with each other, and for a compressive load to be applied and maintained between the bone fragments. Compressive strain between bone fragments has been found to accelerate the healing process in accordance with Wolf's Law.

Broken bones can be rejoined using screws, staples, plates, pins, intramedullary devices, and other devices known in the art. These devices are designed to assist the surgeon with reducing the fracture and with creating a compressive load between the bone fragments. Screws are typically manufactured from either titanium or stainless steel alloys and may be lag screws or headless screws. Lag screws have a distal threaded region and an enlarged head. The head contacts the cortical bone surface and the threaded region reduces the fracture and generates a compressive load. Headless screws typically have a threaded proximal region and a threaded distal region. A differential in thread pitch between the two regions generates compression across the fracture site. There also exist fully threaded headless compression screws that have a thread pitch differential over the length of the thread.

While the aforementioned fracture fixation devices designed to bring the bone fragments into close proximity and to generate a compressive load between the bone fragments, these fracture fixation devices do not always succeed in accomplishing this objective. Among other things, the distal thread and proximal head on lag screws, and the differential pitch on headless bone screws, are generally able to reduce gaps between bone fragments and to create initial compressive loads across the fracture line; however, it is widely reported that this initial compressive load dissipates rapidly as the bone relaxes and remodels around the screw threads. As a result, the compressive load is not maintained for the full duration of the healing process.

Thus there exists a clinical need for fixation devices that are able to generate a compressive load, and maintain that compressive load for a prolonged period of time while healing occurs.

SUMMARY OF THE INVENTION

The present invention provides a novel fixation device which is able to bring bone fragments into close proximity with one another, generate a compressive load, and maintain that compressive load for a prolonged period of time while healing occurs.

Among other things, the present invention comprises the provision and use of a novel compression screw manufactured from a material having a low modulus of elasticity, e.g., an alloy such as Ti—Nb—Zr, Ti—Mo—Zr—Fe or Nitinol, preferably having a modulus of elasticity of less than about 90 GPa. In one preferred form of the invention, the low modulus material is Nitinol, which is preferred because of its low modulus of elasticity and because it exhibits shape memory and/or superelastic properties. Nitinol is capable of being strained elastically up to about 2% and also superelastically up to about 8%. Nitinol per ASTM F2063 is particularly preferred because of its known biocompatibility. The novel compression screw is designed to engage bone fragments on either side of the fracture line and to generate compression between the bone fragments.

In one form of the invention, the novel compression screw comprises a headless screw having a proximal threaded region and a distal threaded region. The pitch of the thread on the proximal threaded region is finer (i.e., more threads per inch) than the pitch of the thread on the distal threaded region. This thread pitch differential reduces fractures and generates compression between the bone fragments. The geometry of the thread on the proximal threaded region and the geometry of the thread on the distal threaded region are preferably mirrored so as to create a "book-end" effect that increases the compression-holding capabilities of the compression screw (e.g., the geometry of the thread on the proximal threaded region is inclined in the proximal direction and has a flat surface in the distal direction wherein the flat surface is substantially perpendicular to the longitudinal axis of the compression screw, and the geometry of the thread on the distal threaded region is mirrored, being inclined in the distal direction and having a flat surface in the proximal direction wherein the flat surface is substantially perpendicular to the longitudinal axis of the compression screw).

The proximal threaded region and the distal threaded region of the compression screw are connected by a central bridge region. The central bridge region can be strained and reversibly elongated (i.e., stretched) through the elastic limit of the material used to form the compression screw, e.g., up to about 8% strain where the compression screw is formed out of a shape memory or superelastic alloy (e.g., Nitinol). It may be beneficial for the central bridge region to be cannulated to control the cross-sectional area of the central bridge region of the compression screw, and thus control the amount of force required to elongate the central bridge region of the compression screw (and hence control the amount of force generated by the central bridge region as the elastically-stretched central bridge region returns to its unstrained state). Additionally, such cannulation allows the compression screw to be implanted using a k-wire for guidance.

It should be appreciated that the low modulus compression screw strains as a compressive force is generated between bone fragments, so that an equivalent tensile force is generated within the compression screw. Thus, depending on the stress-strain relationship of the material which is used to form the compression screw, the tensile force experienced by the compression screw may cause the central bridge region of the compression screw to be strained and axially elongated (i.e., stretched) during implantation. When the compression screw is manufactured from shape memory or superelastic Nitinol, the compression screw may be strained and reversibly elongated up to about 8%.

For low modulus alloys (e.g., Ti—Nb—Zr, Ti—Mo—Zr—Fe or Nitinol, preferably having a modulus of less than about 90 GPa), the elongation of the central bridge region may be limited to the linear elastic region of the stress-strain relationship of the material which is used to form the compression screw. For shape memory or superelastic alloys (e.g., Nitinol), this elongation may be limited to the stress-strain relationship of the austenitic region of the material (e.g., about 2% strain) or, if the compression screw is strained further, the compression screw may undergo a transformation from austenite into stress-induced martensite and hence may be able to be strained and recover from up to about 8% strain.

Following implantation (i.e, after the compression screw has been implanted into the bone and thus strained), the strained central bridge region of the compression screw will attempt to recover from its stretched state and return to its original unstrained (i.e., unstretched) state. In other words, following implantation, the stretched compression screw will attempt to contract back to its unstretched state (i.e., to recover from the strain induced by setting the compression screw in bone). This action provides additional, therapeutic compression to the bone fracture which is maintained even as the bone relaxes and remodels around the threads of the compression screw, whereby to provide superior healing.

In another form of the invention, the novel compression screw comprises a lag screw having a distal threaded region and an enlarged head, and a central bridge connecting the distal threaded region and the enlarged head, wherein the central bridge can be strained and reversibly elongated through the elastic limit of the material which is used to form the compression screw.

In one preferred form of the invention, there is provided a compression screw comprising:

a shaft, a screw thread formed on the shaft at a distal location, and a bone-engaging feature formed on the shaft at a proximal location, wherein at least a portion of the shaft disposed between the screw thread and the bone-engaging feature is capable of being reversibly axially stretched; and wherein the reversible axial stretching of the shaft occurs during implantation of the compression screw and is caused by the distal thread axially stretching the compression screw while the proximal bone engaging feature resists axial displacement.

In another preferred form of the invention, there is provided a compression screw comprising:

a shaft, a screw thread formed on the shaft at a distal region, and a screw thread formed on the shaft at a proximal region, wherein the pitch of the thread at the proximal region is finer than the pitch of the thread at the distal region, and wherein at least a portion of the shaft disposed between the proximal thread and the distal thread is capable of being reversibly axially stretched; and wherein the reversible axial stretching of the shaft occurs during implantation of the compression screw and is caused by the differential between the pitch of the proximal thread and the pitch of the distal thread generating a sufficient axial load.

In another preferred form of the invention, there is provided a method for treating a fracture, the method comprising:

providing a compression screw;

inserting the compression screw into bone, whereby when the compression screw is threaded into the bone so that a distal thread and a proximal bone-engaging feature both engage the bone, sufficient axial stress is created in the central shaft region of the compression screw to stretch that central shaft region, whereby when the proximal bone-engaging feature of the compression screw engages the bone, the compression screw extends across the fracture and the central shaft region has been reversibly stretched up to 8%; and following implantation, allowing the compression screw to apply compression across the fracture as the central shaft region attempts to recover the generated strain.

In another preferred form of the invention, there is provided a method for treating a fracture, the method comprising:

providing a headless compression screw;

inserting the headless compression screw into bone, whereby when the headless compression screw is threaded into the bone, a differential in thread pitch creates sufficient axial stress in the central shaft region of the headless compression screw to stretch that central shaft region, whereby when the proximal thread of the headless compression screw is fully threaded into the bone, the headless compression screw extends across the fracture and the central shaft region has been reversibly stretched up to 8%; and following implantation, allowing the headless compression screw to apply compression across the fracture as the central shaft region attempts to recover the generated strain.

In another preferred form of the invention, there is provided a compression screw comprising:

a shaft capable of being stretched, said shaft having a proximal end and a distal end, said proximal end of said shaft comprising a bone-engaging feature and said distal end of said shaft comprising a distal screw thread, and said proximal end of said shaft comprising a drive feature for turning said shaft;

wherein inserting said compression screw into bone across a fracture line generates a force, and wherein said force generates a stress in said shaft that causes said shaft to stretch to less than its elastic limit; and wherein, after said shaft is inserted into a bone, said shaft attempts to foreshorten to its original un-stretched condition, thereby generating and maintaining compression across the fracture line.

In another preferred form of the invention, there is provided a method for treating a fracture, the method comprising:

providing a compression screw comprising:
a shaft capable of being stretched, said shaft having a proximal end and a distal end, said proximal end of said shaft comprising a bone-engaging feature and said distal end of said shaft comprising a distal screw thread, and said proximal end of said shaft comprising a drive feature for turning said shaft; and
wherein inserting said compression screw into bone across a fracture line generates a force, and wherein said force generates a stress in said shaft that causes said shaft to stretch to less than its elastic limit; and
wherein, after said shaft is inserted into a bone, said shaft attempts to foreshorten to its original un-stretched condition, thereby generating and maintaining compression across the fracture line; and
inserting said shaft into a bone across a fracture line.

In another preferred form of the invention, there is provided a compression screw comprising:
a shaft capable of being stretched, said shaft having a proximal end and a distal end, said proximal end of said shaft comprising a proximal screw thread and said distal end of said shaft comprising a distal screw thread, said proximal screw thread having a finer pitch than said distal screw thread, and said proximal end of said shaft comprising a drive feature for turning said shaft;
wherein inserting said compression screw into bone across a fracture line generates a stretching force along the longitudinal axis of said compression screw due to the pitch differential between said distal screw thread and said proximal screw thread, and wherein said stretching force generates a stress in said shaft that causes said shaft to stretch to less than its elastic limit; and
wherein, after said shaft is inserted into a bone, said shaft attempts to foreshorten to its original un-stretched condition, thereby generating and maintaining compression across the fracture line.

In another preferred form of the invention, there is provided a method for treating a fracture, the method comprising:
providing a compression screw comprising:
a shaft capable of being stretched, said shaft having a proximal end and a distal end, said proximal end of said shaft comprising a proximal screw thread and said distal end of said shaft comprising a distal screw thread, said proximal screw thread having a finer pitch than said distal screw thread, and said proximal end of said shaft comprising a drive feature for turning said shaft; and
wherein inserting said compression screw into bone across a fracture line generates a stretching force along the longitudinal axis of said compression screw due to the pitch differential between said distal screw thread and said proximal screw thread, and wherein said stretching force generates a stress in said shaft that causes said shaft to stretch to less than its elastic limit; and
wherein, after said shaft is inserted into a bone, said shaft attempts to foreshorten to its original un-stretched condition, thereby generating and maintaining compression across the fracture line; and
inserting said shaft into a bone across a fracture line.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIG. 1 is a schematic view showing a novel compression screw formed in accordance with the present invention;

FIG. 1A is a schematic side sectional view of the novel compression screw shown in FIG. 1;

FIG. 3 is a partial list of exemplary low modulus alloys;

FIG. 9 shows exemplary compression screw design parameters;

FIG. 10 shows the axial loads generated by a compression screw manufactured according to the compression screw design parameters of FIG. 9;

FIG. 11 shows that a compression screw designed with the compression screw design parameters of FIG. 9 will not tear through typical bone tissue;

DETAILED DESCRIPTION OF THE PREFERRED EMBODIMENTS

Figure 2:
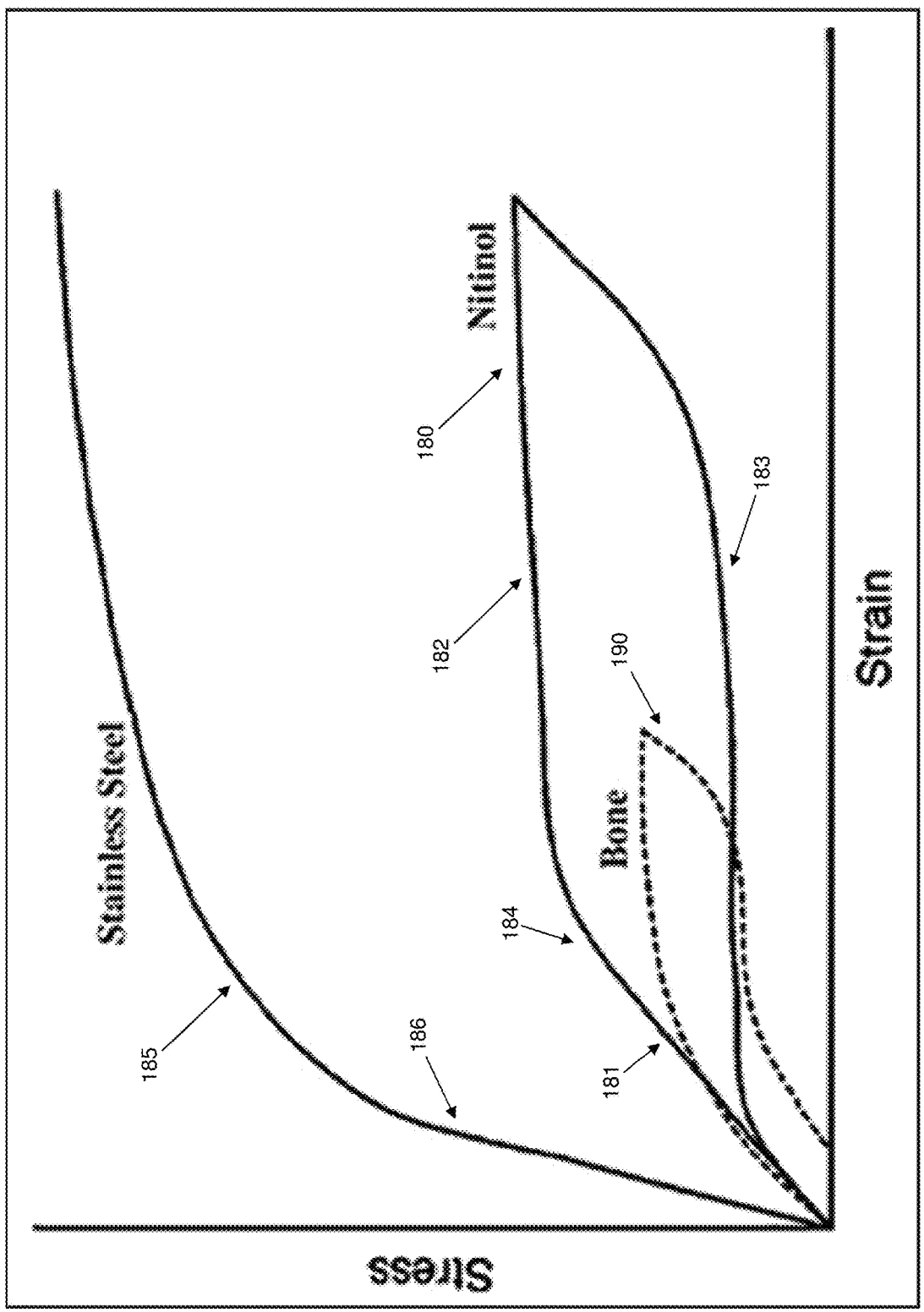
FIG. 2 is a schematic view showing the stress-strain relationship of Nitinol compared to that of stainless steel and bone.

Looking first at FIG. 1, there is shown a novel compression screw 100 for bringing bone fragments into close proximity with one another, generating a compressive load, and maintaining that compressive load for a prolonged period of time while the bone tissue heals. Compression screw 100 is preferably manufactured from a low modulus material (e.g., Ti—Nb—Zr, Ti—Mo—Zr—Fe or Nitinol), preferably with a modulus less than about 90 GPa. In one preferred form of the invention, the low modulus material is Nitinol, which is preferred because of its low modulus of elasticity and because it exhibits shape memory and/or superelastic properties. Nitinol is capable of being strained elastically up to about 2% and also superelastically up to about 8%. Nitinol per ASTM F2063 is particularly preferred because of its known biocompatibility. Compression screw 100 is designed to engage bone fragments and generate compression between the bone fragments.

In one preferred form of the invention, compression screw 100 comprises a shaft 105. In one preferred form of the invention, shaft 105 comprises a proximal threaded region 110 having a proximal screw thread 111 formed thereon and a distal threaded region 120 having a distal screw thread 121 formed thereon. If desired, the distal end of compression screw 100 may be self-cutting or self-tapping (e.g., distal screw thread 121 may be self-cutting or self-tapping). The pitch of proximal screw thread 111 on proximal threaded region 110 is finer than the pitch of distal screw thread 121 on distal threaded region 120. This thread pitch differential reduces the fracture and generates compression. The respective geometries of proximal screw thread 111 and distal screw thread 121 are preferably mirrored, creating a "bookend" effect that increases the compression-holding capabilities of compression screw 100 when compression screw 100 extends across a fracture line in bone (e.g., as seen in FIG. 1A, the geometry of proximal screw thread 111 has an incline 111P in the proximal direction and a flat surface 111D in the distal direction that is substantially perpendicular to the longitudinal axis 125 of compression screw 100; and the geometry of distal screw thread 121 is preferably mirrored, having an incline 121D in the distal direction and a flat surface 121P in the proximal direction that is substantially perpendicular to the longitudinal axis of the compression screw).

Proximal threaded region 110 and distal threaded region 120 are connected by a central bridge region 130. In one preferred form of the invention, central bridge region 130 is hollow. Central bridge region 130 can be strained and reversibly elongated (i.e., stretched) by virtue of the fact that compression screw 100 is manufactured from a low modulus material (e.g., Ti—Nb—Zr, Ti—Mo—Zr—Fe or Nitinol), preferably with a modulus less than about 90 GPa, so that central bridge region 130 may be elastically stretched up to about 1-2% (and, where the low modulus material is Nitinol, may be elastically stretched up to about 8% using the shape memory or superelastic properties of Nitinol). The cross-sectional area of central bridge region 130 is engineered to allow that region of the compression screw to be elastically stretched during implantation and to thereafter recover, i.e., so as to attempt to shorten in order to recover its initial length after being stretched during implantation. The stretching and recovery force is proportional to the cross-sectional area of central bridge region 130. Thus, the cross-sectional area of compression screw 100 is engineered so that the loads created during recovery (i.e., post-implantation shortening) are not so great as to cause the screw's threads to shear through the bone.

By screwing compression screw 100 across the fracture line of a fractured bone, with distal screw thread 121 disposed on one side of the fracture line and with proximal screw thread 111 disposed on the other side of the fracture line, the pitch differential between proximal screw thread 111 and distal screw thread 121 generates compression between the bone fragments, and thus imparts an axial load on central bridge region 130. This axial load generates stress in central bridge region 130. Compression screw 100 is designed such that this stress causes the central bridge region 130 to reversibly axially stretch during implantation, and to attempt to axially contract after implantation.

Figure 3:
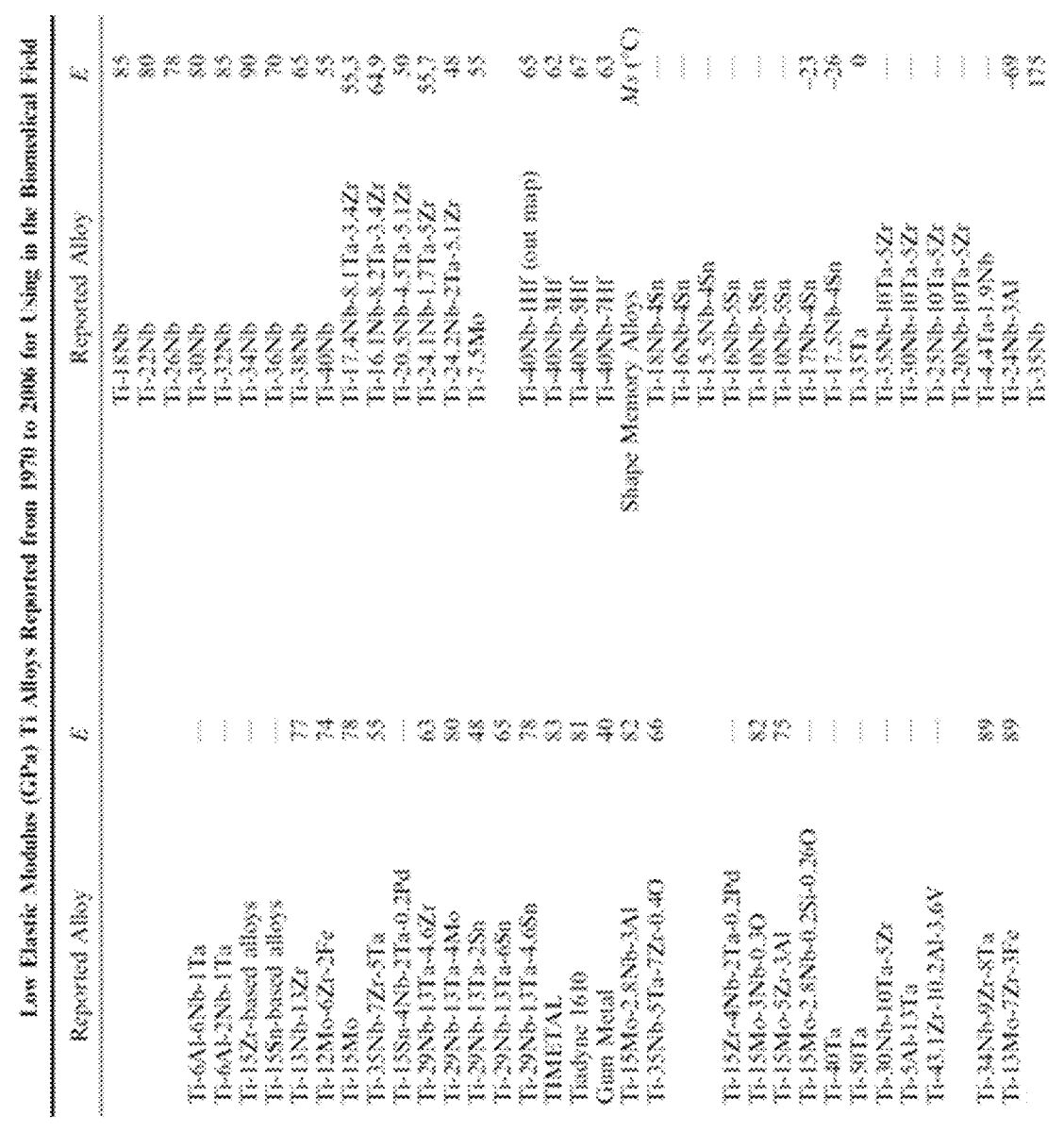

Looking now at FIGS. 2 and 3, the stress-strain relationship of Nitinol (180), stainless steel (185), and bone (190) are shown. As can be seen in FIG. 2, the modulus of stainless steel (represented by the slope of region 186) is significantly greater than the modulus of Nitinol (represented by the slope of region 181). Thus, Nitinol is a low modulus alloy and will experience greater strain at a given stress compared to stainless steel, or compared to other higher modulus alloys. Other low modulus alloys include Ti-13Nb-13Zr, Ti-12Mo-6Zr-2Fe, Ti-15Mo, Ti-16Nb-10Hf, Ti-15Mo-5Zr-3Al, Ti-15Mo-2.8Nb-0.2Si-0.260, Ti-35Nb-7Zr-5Ta, and Ti-29Nb-13Ta-4.7Zr. A more complete (but not exhaustive) list of low modulus alloys is provided in FIG. 3. In general, for the purposes of the present invention, the term "low modulus alloys" is intended to mean alloys having a modulus of elasticity less than about 90 GPa.

Unlike other low modulus alloys, Nitinol also exhibits a stress-strain hysteresis whereby, at a critical stress, the material will undergo large elastic deformations and, upon releasing that stress, the material will recover to its unstrained condition.

Looking more closely at the stress-strain relationship of Nitinol (FIG. 2), region 181 refers to the austenitic modulus of Nitinol. Region 182 of the Nitinol stress-strain graph refers to the "Upper Plateau". In this region, the material undergoes a stress-induced transformation of austenite to martensite. This occurs at a nearly constant stress level, referred to as the "Upper Plateau Stress". This transformation allows the material to be reversibly strained up to about ~8% strain. Releasing the stress allows the material to recover along region 183. This is referred to as the "Lower Plateau". In this region, the material is recovering strain along a nearly linear "Lower Plateau Stress".

Figure 4:
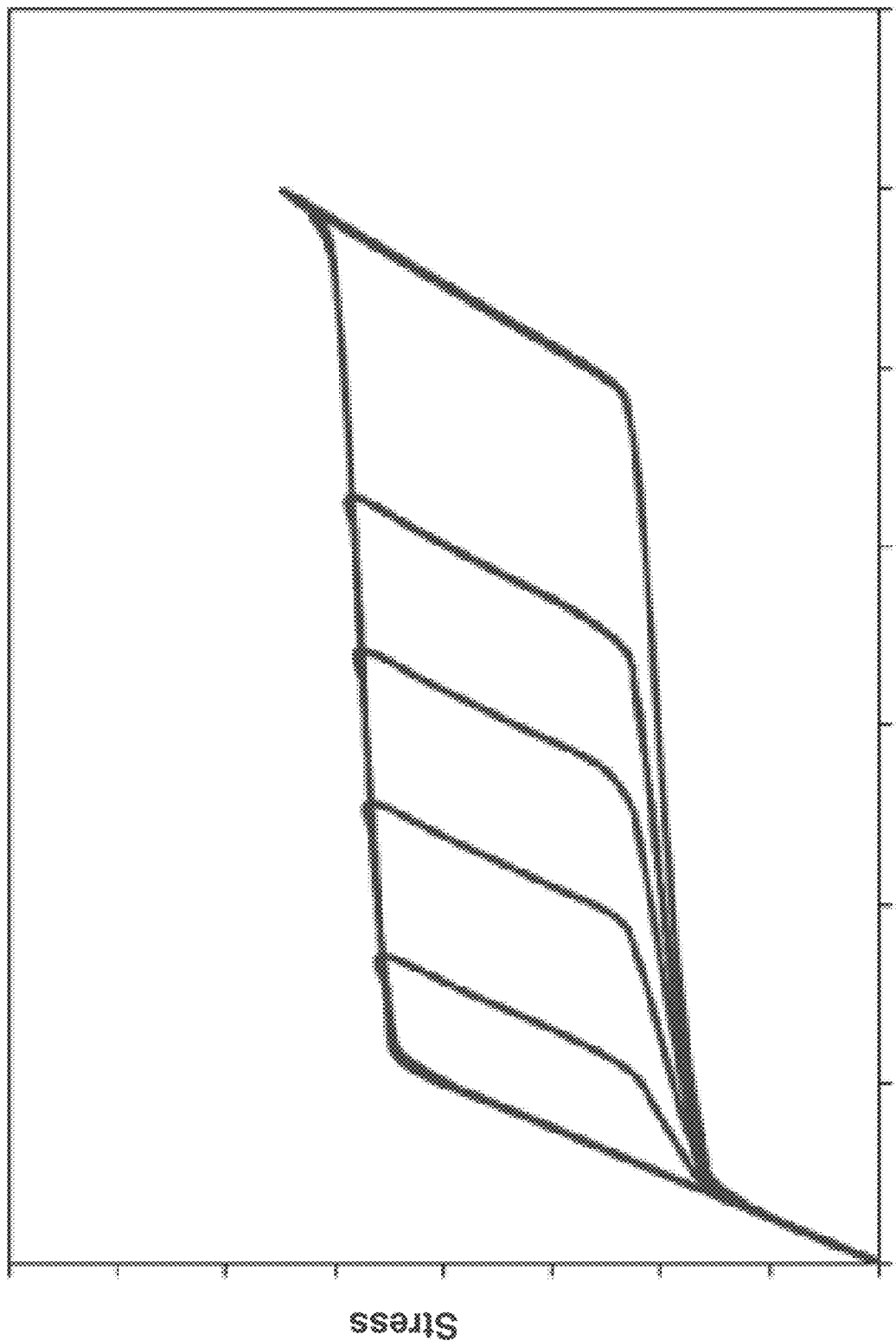
FIG. 4 is a schematic view showing the stress-strain relationship for Nitinol when it is strained to different levels.

It should be appreciated that a compression screw 100 formed out of Nitinol can be strained during implantation to any point on region 181 or 182. It should also be appreciated, and now looking at FIG. 4, that if the Nitinol compression screw 100 is stretched sufficiently so as to allow the Nitinol to at least partially undergo the transformation to martensite, the compression screw will recover strain at a Lower Plateau Stress regardless of the extent to which the compression screw is stretched (as long as it is stretched to less than about 8%).

The compression generated between the bone fragments is equivalent to a tensile load in the compression screw. For low modulus materials, compression screw 100 is engineered to be strained during insertion into the bone but not to exceed the elastic limit of the material out of which the compression screw is formed. Compression screw 100 will then attempt to shorten to its original length, generating and maintaining therapeutic compression across the fracture line.

For a compression screw made from Nitinol, if during insertion the compression screw is not strained beyond the point where stress-induced martensite is created (i.e., so that the material remains in its austenitic state, in the region 181 shown in FIG. 2), which is typically less than about 2% strain, central bridge region 130 of compression screw 100 will strain according to the austenitic modulus of the material. Nitinol's austenitic modulus is ~80 GPa while the modulus of 316 stainless steel is ~190 GPa. Thus, a Nitinol compression screw 100 will strain almost 3× more than a similar compression screw formed out of stainless steel. After fully threading compression screw 100 into the bone, the contracting central bridge region 130 can provide additional compression to the bone fracture as the compression screw seeks to shorten ("foreshorten") to its original unstrained length.

If during insertion, compression screw 100 is strained sufficiently so as to create stress-induced martensite (i.e., so that the material is in the region 182 shown in FIG. 2), the contracting central bridge region 130 can be strained up to about 8%. After fully threading compression screw 100 into the bone, contracting central bridge region 130 will then attempt to recover to its original length along its Lower Plateau Stress (region 183 in FIG. 2) and provide additional compression to the bone fracture.

Compression screw 100 comprises a drive feature 140 (e.g., a hexalobe) in proximal threaded region 110 for engagement by an appropriate driver (not shown) of the sort well known in the art, whereby to turn compression screw 100 (e.g., into bone).

Figure 5:
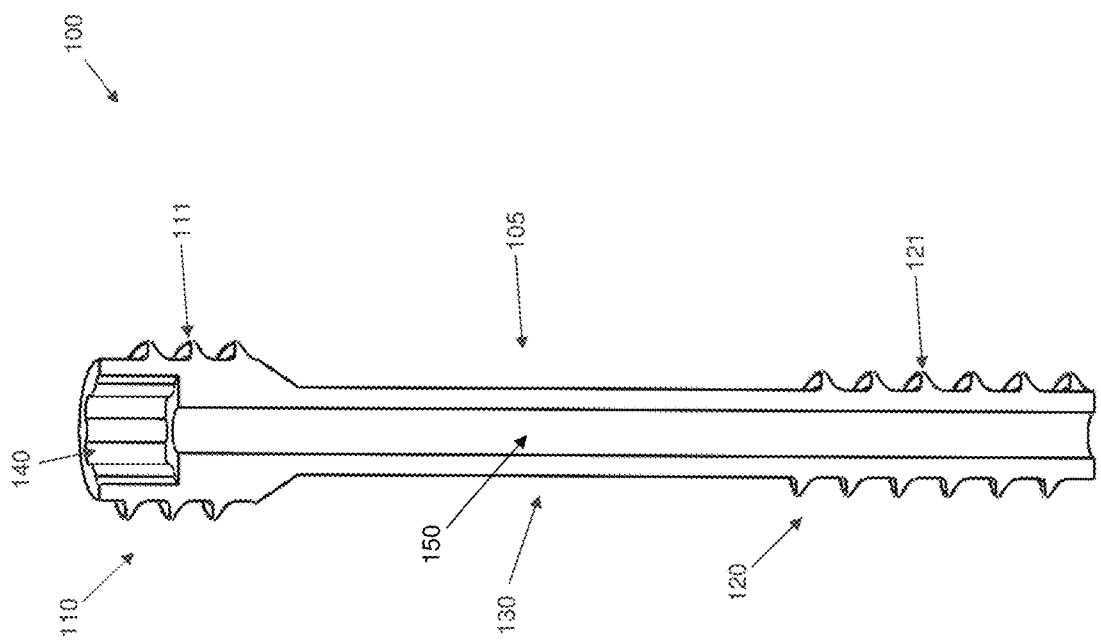
FIG. 5 is a schematic view showing the internal features of the compression screw of FIG. 1.

Compression screw 100 may comprise a central lumen 150 (FIG. 5) which extends the length of the compression screw. It is generally preferred to provide compression screw 100 with a central lumen 150 extending the entire length of the compression screw so that the compression screw can be set over a k-wire.

Thus, in one preferred form of the invention, compression screw 100 is formed out of a low modulus material (e.g., Ti—Nb—Zr, Ti—Mo—Zr—Fe or Nitinol), preferably with a modulus less than about 90 GPa, so that central bridge region 130 may be elastically stretched up to about 1-2% (and, where the low modulus material is Nitinol, may be elastically stretched up to about 8% using the shape memory or superelastic properties of Nitinol). Compression screw 100 comprises distal screw threads 121 and proximal screw threads 111 connected by a central bridge region 130, with distal screw threads 121 and proximal screw threads 111 having a pitch differential such that advancing compression screw 100 across a fracture line induces stress in central bridge region 130 and causes elastic strain (i.e., stretching) in central bridge region 130. After implantation, central bridge region 130 will attempt to contract, thereby supplying additional compression to the bone fracture as the bone relaxes and remodels around the compression screw. As a result, compression screw 100 is able to bring bone fragments into close proximity with one another, generate a compressive load, and maintain that compressive load for a long period of time while healing occurs. In one preferred form of the invention, compression screw 100 is cannulated, so that the compression screw can be set over a k-wire. In addition, such cannulation can be used to regulate the cross-sectional area of central bridge region 130, whereby to control the amount of strain created in central bridge region 130 during implantation of compression screw 100.

Controlling the Compression Force Generated During Implantation of the Compression Screw It should be appreciated that the force required to reversibly strain central bridge region 130, and the recovery force generated by the contracting central bridge region 130, should be less than the pullout force in bone for the proximal screw thread 111 and distal screw threads 121, so that compression screw 100 does not "tear through" the bone tissue. Thus, compression screw 100 is engineered so as to limit the force required to reversibly strain central bridge region 130 and to limit the force generated by the contracting central bridge region 130. The force which strains central bridge region 130 (and which is stored in the strained central bridge region 130) can be controlled by modulating the screw's material properties and/or the screw's geometry.

Figure 6:
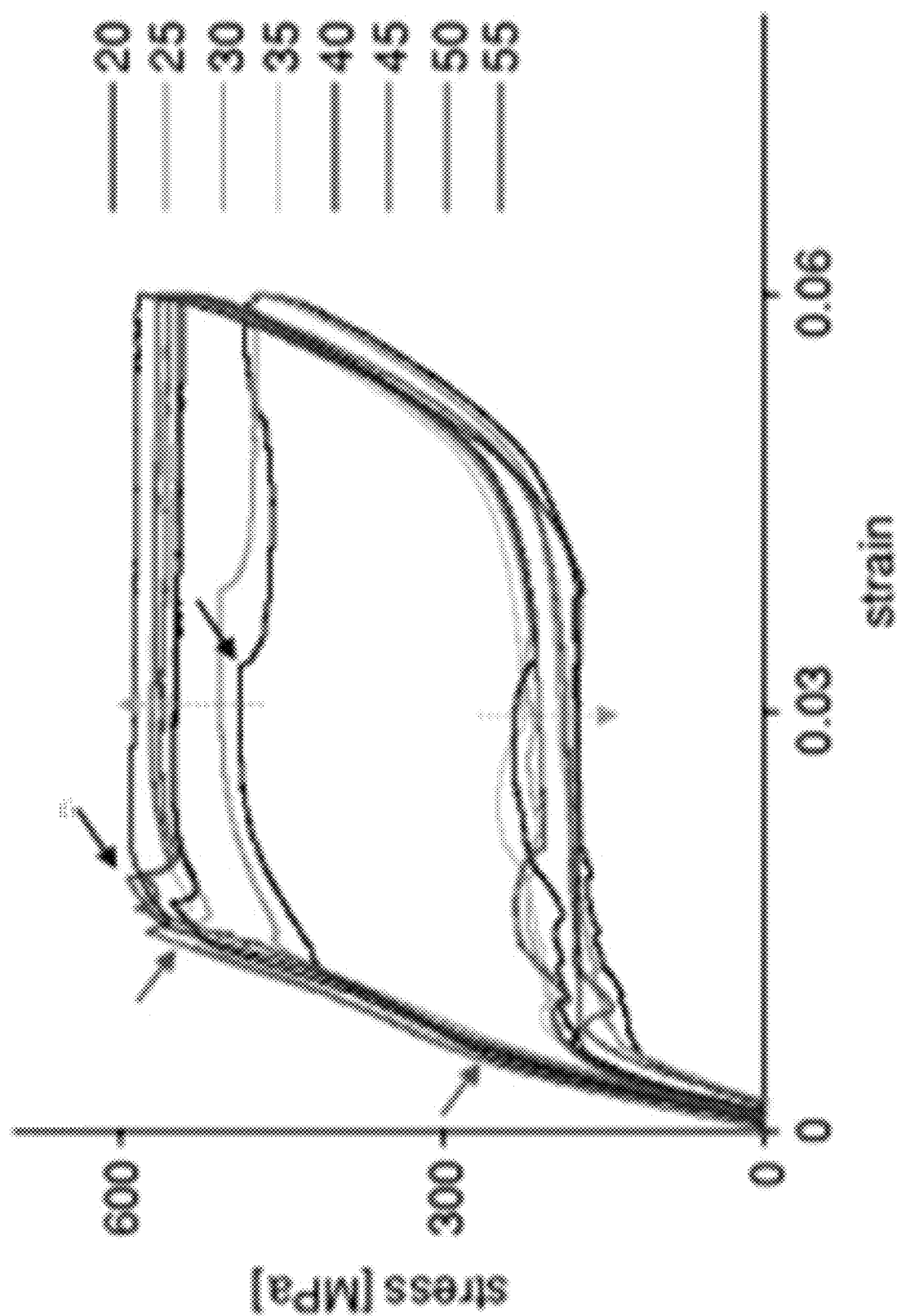
FIG. 6 is a schematic view showing the effect of cold work on the stress-strain behavior of Nitinol.

FIG. 6 shows how the percentage of cold work in the material used to form compression screw 100 (e.g., Nitinol) affects the Upper Plateau Stress and the Lower Plateau Stress of the material (e.g., when the Nitinol is exhibiting its shape memory or superelastic properties). As the percentage of cold work increases, the Upper Plateau Stress increases and the Lower Plateau Stress decreases. A Nitinol compression screw should, preferably, have between 0% and 55% cold work to appropriately control the Upper Plateau Stress and the Lower Plateau Stress. Thus, in one preferred form of the invention, where compression screw 100 is formed out of Nitinol, the percentage of cold work in the Nitinol is approximately 55% or less. In one preferred form of the invention, there is provided a compression screw formed out of Nitinol (cold worked up to 55%, with at least 180 ksi Ultimate Tensile Strength (1,241 Mpa) for increased strength, while having a modulus of elasticity of less than 90 GPa) and engineered to have a differential thread pitch force large enough to elastically (reversibly) stretch the screw's cold worked bridge yet have a thread gripping power sufficient so that the compression screw does not strip through the bone.

Figure 7:
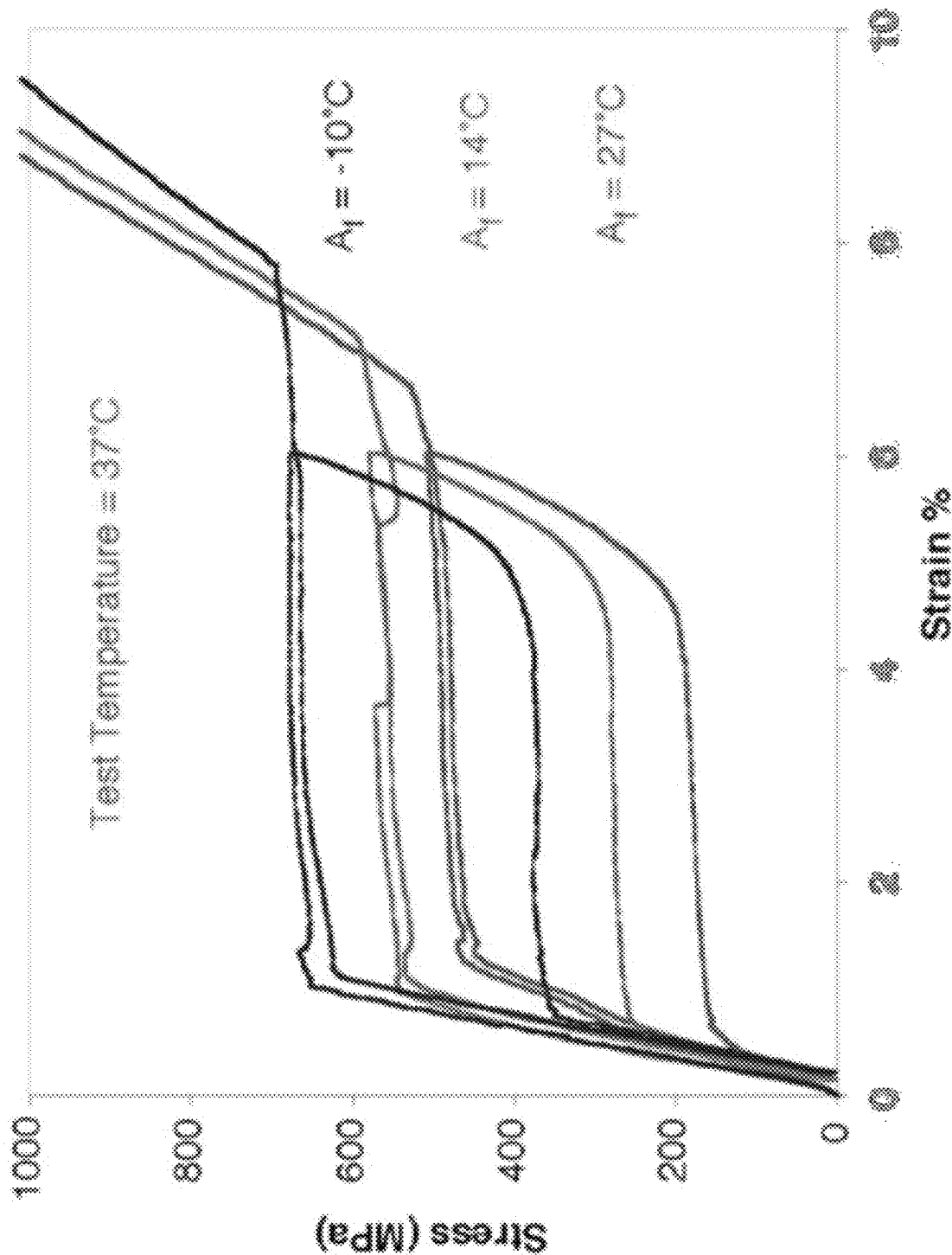
FIG. 7 is a schematic view showing the effect of temperature differential (between the body that the compression screw will be implanted into and the austenite finish temperature of the material used to form the compression screw) on the stress-strain behavior of Nitinol.

Another material property that affects the Upper Plateau Stress (and the Lower Plateau Stress) is the temperature differential between the body in which the compression screw will be implanted (assumed to be 37° C.) and the austenite finish temperature of the material (e.g., Nitinol) out of which compression screw 100 is formed. FIG. 7 shows this relationship. A smaller temperature differential between body temperature and the austenite finish temperature of the Nitinol will result in a lower Upper Plateau Stress and a Lower Plateau Stress. The material that the compression screw is made out of (e.g., Nitinol) should, preferably, have an austenite finish temperature of greater than 0° C., resulting in a temperature differential of less than 37° C. The material's austenite finish temperature can be adjusted through heat treatments of the sort well known in the art of metallurgy.

Screw geometry also affects the axial load that is required to stretch central bridge region 130 (and hence the recovery force generated by contracting central bridge region 130). The cross-sectional area of central bridge region 130 directly affects this. When the compression screw is made out of Nitinol (or another material which exhibits shape memory and/or superelastic characteristics), as the cross-sectional area of central bridge region 130 increases, so does the force required to exceed the Upper Plateau Stress. It should be appreciated that central bridge region 130 may be cannulated to decrease the cross-section of the central bridge region, and thus decrease both the force required to stretch compression screw 100 and the force generated as the compression screw thereafter contracts.

The threads of compression screw 100 are critical for resisting the forces that would "tear through" the bone, and thus proximal screw thread 111 and distal screw thread 121 are engineered so as to allow central bridge region 130 to experience the stresses sufficient to appropriately stretch central bridge region 130 (but not to overstretch central bridge region 130). The height of the threads, the number of threads per inch (pitch), and the geometry of the threads are all critical to the ability of compression screw 100 to generate adequate strain for therapeutic purposes while not generating excessive strain which would result in "tear through" in the bone. Proximal screw thread 111 and distal screw thread 121 may be of different lengths. The length of distal screw thread 121 may be equal to or greater than the length of proximal screw thread 111. The length of distal screw thread 121 should be at least 20% of the total length of compression screw 100. Additionally, the height of distal screw thread 121 should be equal to or greater than the height of proximal screw thread 111.

The geometry of distal screw thread 121 may also be mirrored with respect to the geometry of proximal screw thread 111. More particularly, and as seen in FIG. 1A, the geometry of proximal screw thread 111 on proximal threaded region 110 may have an incline 111P in the proximal direction and a flat surface 111D in the distal direction that is substantially perpendicular to the longitudinal axis 125 of compression screw 100, and the geometry of distal screw thread 121 on distal threaded region 120 may be mirrored, having an incline 121D in the distal direction and a flat surface 121P in the proximal direction that is substantially perpendicular to the longitudinal axis 125 of compression screw 100. This creates threaded regions where the load-bearing thread faces are nearly perpendicular to the longitudinal axis of compression screw 100. The resulting thread form has high shear strength.

It will be appreciated that the various parameters of the novel compression screw can be engineered so as to limit the compressive force generated by the compression screw to a level which is below a given bone shear stress limit. In general, the novel compression screw is engineered to limit the compressive force generated by the compression screw to approximately 65 MPa, which is typical of the bone shear stress limit of healthy cortical bone. However, the novel compression screw can be engineered to limit the compressive force to a lower or higher limit, e.g., to 25 MPa in poor quality/osteoporotic bone, or up to 100 MPa in strong/athletic cortical bone.

Thus, in one form of the present invention, the invention comprises the provision and use of a novel compression screw for generating and maintaining a compressive load across a fracture line in bone as the bone relaxes and remodels around the compression screw during healing, wherein the novel compression screw comprises:

a shaft having a distal end, a proximal end and a central bridge region extending therebetween, the shaft being formed out of a material having a low modulus of elasticity;

a distal screw thread formed on the distal end of the shaft; and a proximal bone-engaging feature formed on the proximal end of the shaft;

wherein:
(i) the material out of which the shaft is formed,
(ii) the configuration of the central bridge region of the shaft,
(iii) the configuration of the distal screw thread, and
(iv) the proximal bone-engaging feature, are all selected such that when the compression screw is turned into bone so that the distal screw thread is disposed on one side of the fracture line and the proximal bone-engaging feature is disposed on the other side of the fracture line, the forces imposed on the compression screw during the process of implantation into the bone cause the compression screw to longitudinally stretch, but only to an extent less than its elastic limit, such that after implantation into the bone the compression screw generates and maintains compression across the fracture line as the compression screw attempts to foreshorten to its original length, with the compression being maintained as the bone relaxes and remodels around the compression screw during healing.

In one preferred form of the invention, the compression screw is formed out of material having a modulus of elasticity of less than about 90 GPa.

And in one preferred form of the invention, the compression screw is formed out of Nitinol.

And in one preferred form of the invention, the proximal bone-engaging feature comprises a proximal screw thread.

And in another preferred form of the invention, the proximal bone-engaging feature comprises an enlarged head.

And in one preferred form of the invention, the compression screw is cannulated.

Use of the Novel Compression Screw

Figure 8:
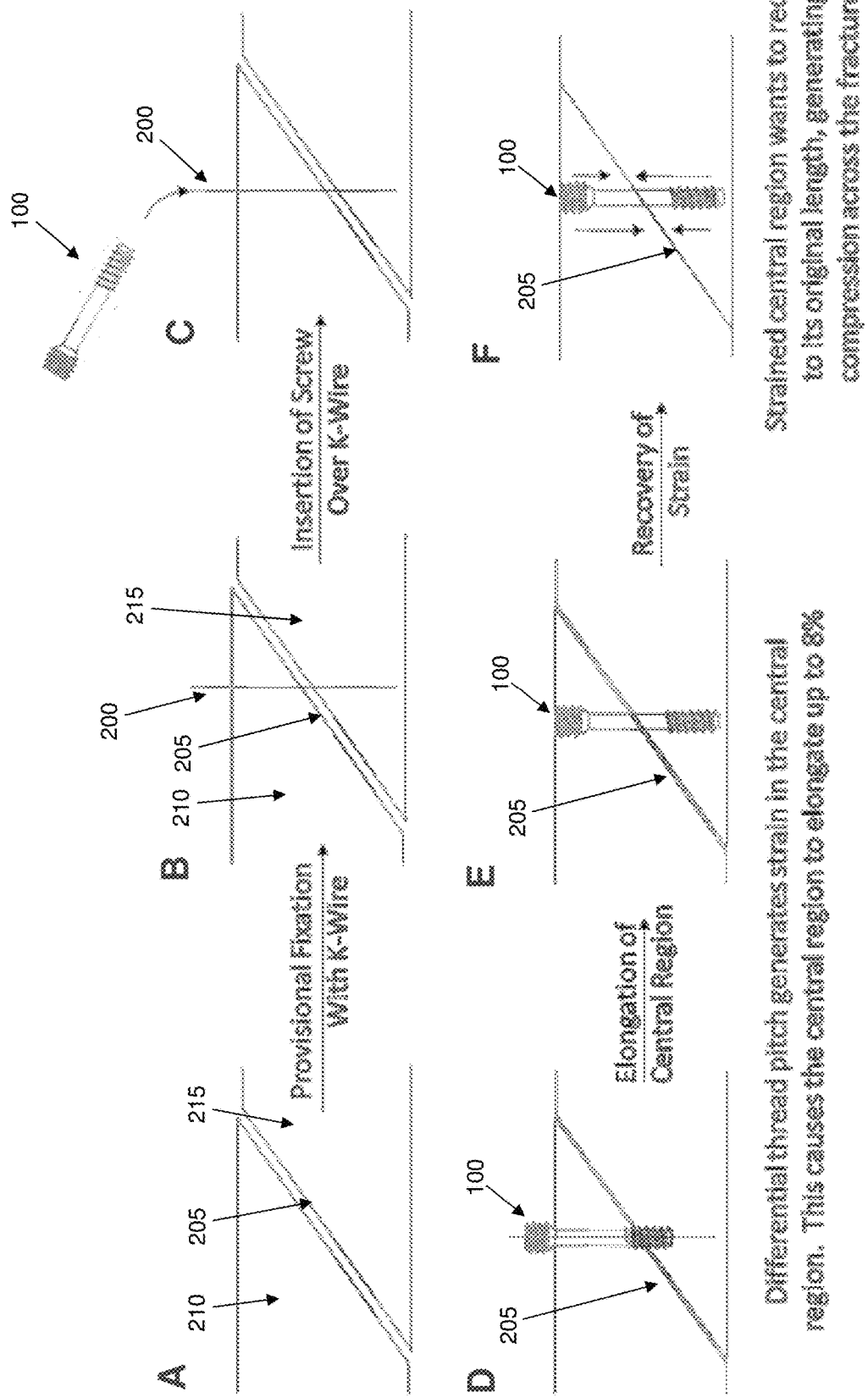
FIG. 8 is a schematic view showing how the compression screw of FIG. 1 may be used to treat a fracture.

Looking now at FIG. 8, compression screw 100 can be used to aid in the healing of fractured bone. More particularly, in one preferred form of the invention, a k-wire 200 is inserted across a fracture line 205 to provisionally stabilize bone fragments 210 and 215. Compression screw 100 (formed out of a low modulus material such as Nitinol) is then slid over k-wire 200 and threaded into bone fragments 210 and 215 so that compression screw 100 extends across fracture line 205. The differential pitch between proximal screw thread 111 and distal screw thread 121 creates compression across fracture line 205 and reduces the fracture. As compression screw 100 is thoroughly countersunk into the bone, the pitch differential between proximal screw thread 111 and distal screw thread 121 generates sufficient axial tension in central bridge region 130 to reversibly stretch central bridge region 130 up to about 8%. With each rotation of the compression screw, distal screw thread 121 advances into the bone faster than proximal screw thread 111. This thread differential (and hence thread advancement differential) is what creates axial tension in central bridge region 130 of compression screw 100. K-wire 200 is then removed.

With implantation of compression screw 100 complete, compression screw 100 will attempt to foreshorten to its pre-strained (i.e., pre-stretched) condition. Inasmuch as proximal screw thread 111 and distal screw thread 121 of compression screw 100 are disposed in bone fragments 210, 215, respectively, such that central bridge region 130 extends across fracture line 205, the foreshortening of compression screw 100 will generate additional compressive load across fracture line 205, thereby enhancing healing.

As noted above, compression screw 100 is provided with a drive feature 140, whereby to turn compression screw 100 into bone. Drive feature 140 can be a standard screw drive feature such as a drive slot, a Philips (cruciform) drive configuration, a hex or hexalobe recess, or other engagement feature of the sort well known in the art.

Example 1

Nitinol Compression Screw that Will Strain at Upper Plateau

Looking now at FIG. 9, exemplary design properties of a novel compression screw 100 are shown. These values are intended to be exemplary only and not limiting, though one skilled in the art will appreciate their clinical relevance.

Looking now at FIG. 10, the tensile forces generated by the differential thread pitch of compression screw 100 are shown. The differential thread pitch generates a compressive load between bone fragments which also creates an axial load in central bridge region 130 of compression screw 100. This compression screw is inserted into the bone with a torque of 750 N-mm, which is less than the torsional yield strength of the screw (>800 N-mm). Using the following equation:

$$T = cDF$$

where:
T=Torque required
F=Tension desired
D=Nominal screw diameter
c=Coefficient of friction (assumed to be 0.1)

proximal screw thread 111 generates an axial load of approximately 1744 N, and distal screw thread 121 generates an axial load of approximately 2381 N. Thus, there is an axial load differential of 637 N between the axial load generated by proximal screw thread 111 and the axial load generated by distal screw thread 121. This axial load differential imposes tension on central bridge region 130 of compression screw 100. Central bridge region 130 of this compression screw has a cross-sectional area of 1.51=². This generates a stress of 421 MPa which is greater than the Upper Plateau Stress (400 MPa) of the material out of which compression screw 100 is formed (e.g., shape memory or superelastic Nitinol). Thus central bridge region 130 will undergo a transformation to stress-induced martensite and axially elongate. The length of proximal screw thread 111 is 4.5 mm, and the thread pitch differential is 0.15 mm (see, for example, FIG. 9, where proximal screw thread 111 has a pitch of 1.10 mm and distal screw thread 121 has a pitch of 1.25 mm, thereby yielding a thread pitch differential of 1.25 mm−1.10 mm=0.15 mm). Thus, fully inserting compression screw 100 into the bone will cause central bridge region 130 to elongate approximately 0.67 mm or 6.4%. After implantation, compression screw 100 will attempt to axially foreshorten and return to its unstrained length. This action will generate and maintain compression across the fracture line as healing occurs.

Looking now at FIG. 11, the shear stress generated by threaded regions 110, 120 are analyzed to ensure they do not exceed a bone shear stress limit (65 MPa) which is typical of healthy cortical bone. Proximal screw thread 111 generates a shear stress of 64 MPa, and distal screw thread 121 generates a shear stress of 50 MPa. Thus, compression screw 100 will not strip in the bone.

Example 2

Compressive Load Generated by Low Modulus Screw

Figure 12:
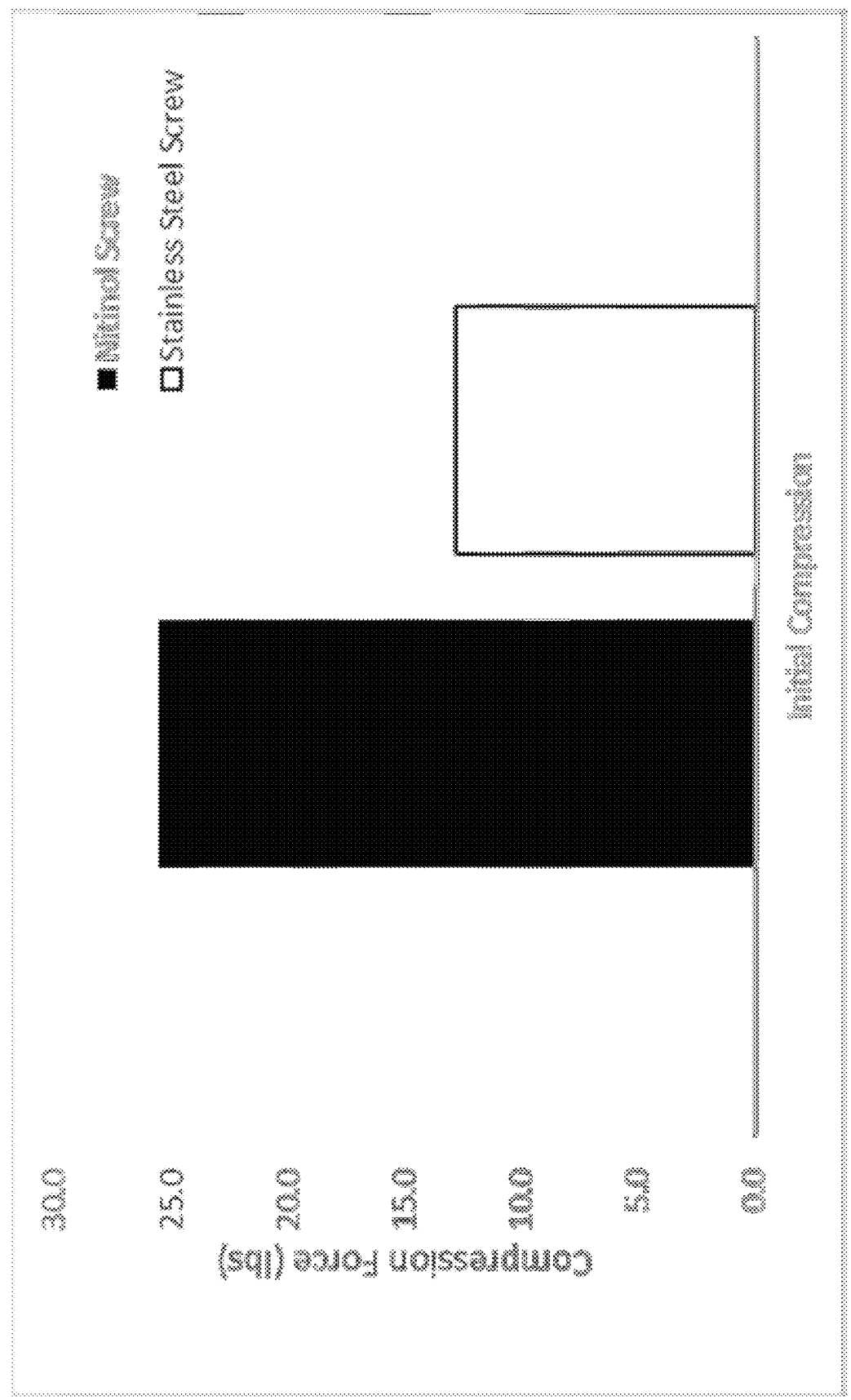
FIG. 12 is a schematic view showing the additional compression that a low modulus compression screw generates, initially after of implantation, compared to a comparable stainless steel compression screw.
Figure 13:
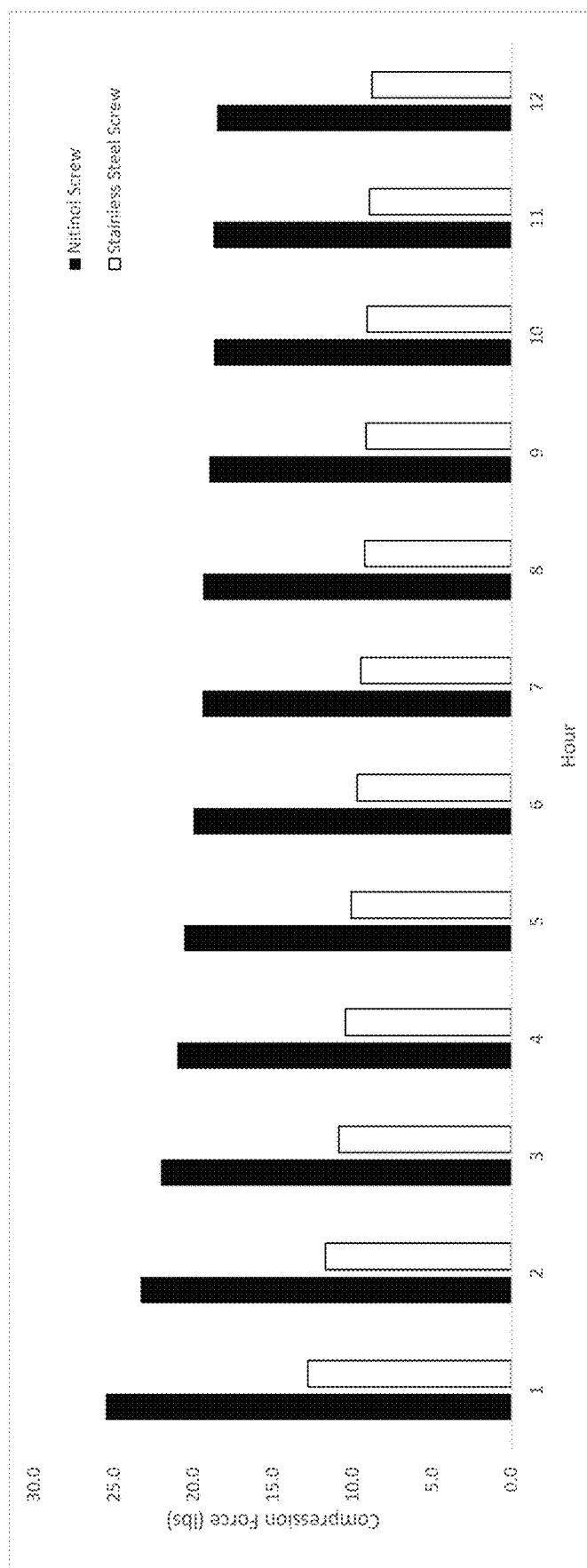
FIG. 13 is a schematic view showing the additional compression that a low modulus compression screw generates, over a 12-hour period, compared to a comparable stainless steel compression screw.

Looking now at FIG. 12, the compressive load generated by a self-compressing low modulus compression screw manufactured from Nitinol (or Ti—Nb—Zr, Ti—Mo—Zr—Fe or other low modulus material), preferably with a modulus less than about 90 GPa, is shown and compared to a traditional compression screw manufactured from stainless steel. Both compression screws are of comparable dimensions and geometries. The compression screw is designed to slightly stretch central bridge region 130 (though not enough to create stress-induced martensite if made from Nitinol) during insertion. Following implantation, as the compression screw attempts to shorten to its original length, the Nitinol compression screw generates nearly twice the compression than that of the comparable stainless steel compression screw. Looking at FIG. 13, it can be seen that the low modulus Nitinol compression screw maintains this compression over a long time period.

Reversible Twisting of the Novel Compression Screw

It should be appreciated that in addition to axial (i.e., longitudinal) elongation, the insertion of novel compression screw 100 can cause elastically reversible twisting of the compression screw. In other words, torqueing novel compression screw 100 during insertion can cause the compression screw to elastically reversibly twist about its longitudinal axis. Thus, after compression screw 100 has been inserted, the compression screw can recover this twist, imparting additional compression across the fracture line. Where the novel compression screw 100 is formed out of a shape memory alloy, the novel compression screw may also have a pre-bias twist from shape setting the compression screw in the same or opposite direction of the threading action. This pre-bias can be recovered by temperature transition after implantation to generate additional compression across the fracture line.

Localized Heat Treating

Compression screw 100 may also be selectively heat treated to locally change the mechanical properties of the compression screw. Thus, central bridge region 130 may be constructed to have a smaller temperature differential between body temperature and austenite finish temperature than proximal and distal threaded regions 110, 120.

Other Compression Screw Configurations

Figure 14:
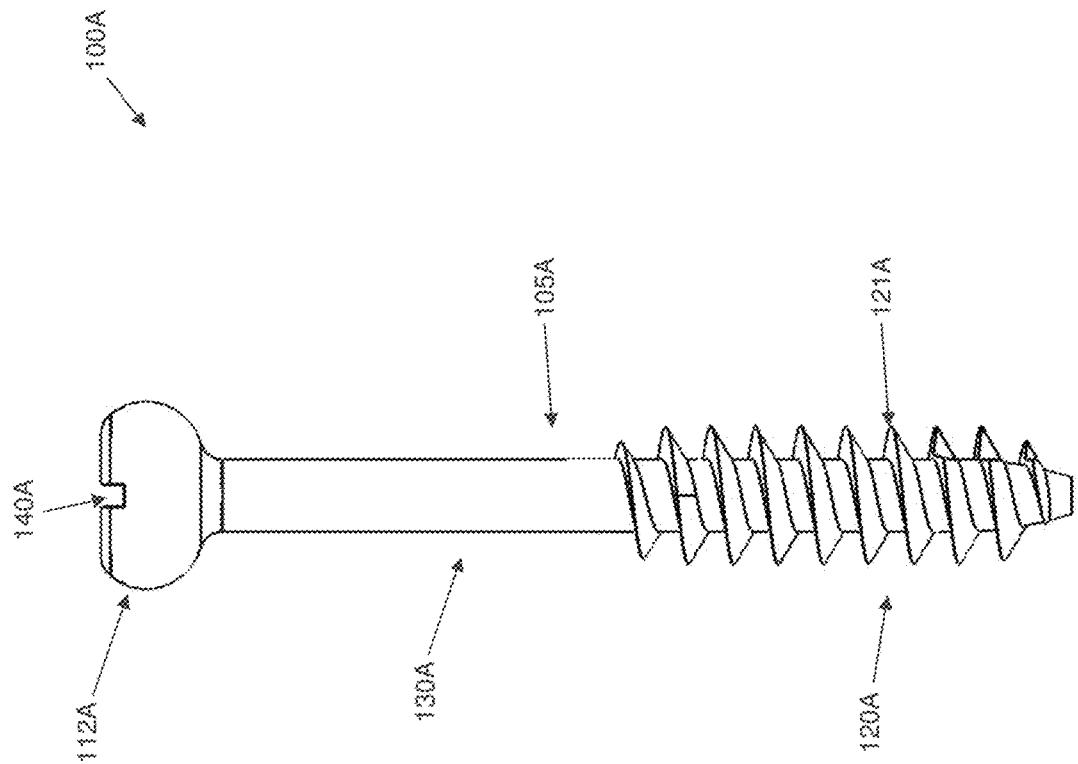
FIG. 14 is a schematic view of a lag-type compression screw formed in accordance with the present invention.

It should be appreciated that the present invention may also be utilized with other compression screw configurations including, but not limited to, headed (i.e., lag-type) compression screws. See, for example, FIG. 14 where a headed compression screw 100A is shown. Compression screw 100A is similar to compression screw 100 previously discussed, except that proximal threaded region 110 and proximal screw thread 111 are replaced by a head 112A. When headed compression screw 100A is tightened into bone, head 112A will abut the bone surface. Further tightening of headed compression screw 100A will advance distal screw thread 121A without advancing head 112A, thereby generating compression between the bone fragments and an axial tension in central bridge region 130A of headed compression screw 100A. Again, this axial tension will reversibly strain central bridge region 130, generating additional compression between bone fragments.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:
1. A compression screw comprising:
a shaft having a longitudinal axis capable of being stretched, said shaft having a proximal end and a distal end, said proximal end of said shaft comprising an external proximal screw thread and said distal end of said shaft comprising a distal screw thread, a pitch of said proximal screw thread is finer than a pitch of said distal screw thread, and said proximal end of said shaft comprises a drive feature for turning said shaft, wherein said compression screw is a single component, wherein said shaft is a single unitary piece of metal that is slotless,
wherein inserting said compression screw into bone across a fracture line is configured to generate a force, and wherein said force is configured to generate a stress in said shaft that causes said shaft to stretch to less than its elastic limit, wherein the shaft is configured to reversibly axially stretch along the longitudinal axis from an original un-stretched condition to a stretched condition, wherein the stretched condition is longer than the original un-stretched condition, and
wherein, after said shaft is inserted into the bone, said shaft is configured to attempt to axially contract along the longitudinal axis to the original un-stretched con- dition, thereby generating and maintaining compression across the fracture line.

2. The compression screw according to claim 1 wherein said shaft comprises a low modulus alloy.

3. The compression screw according to claim 2 wherein said low modulus alloy is a shape memory or superelastic alloy.

4. The compression screw according to claim 3 wherein said shape memory or superelastic alloy comprises Nitinol.

5. The compression screw according to claim 1 wherein said drive feature comprises at least one selected from the group consisting of a slot, a cruciform recess, a hex recess and a hexalobe recess.

6. The compression screw according to claim 1 wherein said distal end of said shaft comprises a self-cutting feature.

7. The compression screw according to claim 1 wherein said external proximal screw thread and said distal screw thread are mirrored so as to increase the compression-holding capabilities of the compression screw.

8. The compression screw according to claim 1 wherein, when said shaft attempts to foreshorten to the original un-stretched condition, it does so at a load which is engineered to be low enough so as not to strip said distal screw thread through the bone.

9. The compression screw according to claim 1 wherein said shaft has a cross-sectional area that is engineered to control the recovery load so as not to cause said distal screw thread to pull through the bone.

10. The compression screw according to claim 1 wherein said distal screw thread and said external proximal screw thread are spaced apart and separated by a portion of said shaft that is threadless.

11. The compression screw according to claim 1 wherein said shaft includes a cannulation that extends from said proximal end of said shaft to said distal end of said shaft.

12. The compression screw according to claim 1 wherein said external proximal screw thread and said distal thread have a cross sectional shape defined by an inclined portion and a flat portion, wherein the flat portion is substantially perpendicular to the longitudinal axis.

13. The compression screw according to claim 1 wherein the proximal end of said shaft that comprises the external proximal screw thread is the most proximal end of the compression screw.

14. A compression screw comprising:
a shaft having a longitudinal axis capable of being stretched, said shaft having a proximal end and a distal end, said proximal end of said shaft comprising an external proximal screw thread and said distal end of said shaft comprising a distal screw thread, said external proximal screw thread having a finer pitch than said distal screw thread, and said proximal end of said shaft comprises a drive feature for turning said shaft, wherein said compression screw is a single component, and said shaft is a single unitary piece of metal that is slotless,
wherein inserting said compression screw into bone across a fracture line is configured to generate a stretching force along the longitudinal axis of said compression screw due to a pitch differential between said distal screw thread and said external proximal screw thread, and wherein said stretching force is configured to generate a stress in said shaft that causes said shaft to stretch to less than its elastic limit, wherein the shaft is configured to reversibly axially stretch along the longitudinal axis from an original un-stretched condition to a stretched condition, wherein the stretched condition is longer than the original un-stretched condition, and
wherein, after said shaft is inserted into the bone, said shaft is configured to attempt to axially contract along the longitudinal axis to the original un-stretched condition, thereby generating and maintaining compression across the fracture line.

15. The compression screw according to claim 14 wherein, when said shaft attempts to foreshorten to the original un-stretched condition, it does so at a load which is engineered to be low enough so as not to strip either said external proximal screw thread or said distal screw thread through the bone.

16. The compression screw according to claim 14 wherein said distal screw thread and said external proximal screw thread are spaced apart and separated by a portion of said shaft that is threadless.

17. The compression screw according to claim 14 wherein said shaft includes a cannulation that extends from said proximal end of the shaft to said distal end of said shaft.

18. The compression screw according to claim 14 wherein said external proximal screw thread and said distal thread have a cross sectional shape defined by an inclined portion and a flat portion, wherein the flat portion is substantially perpendicular to the longitudinal axis.

19. The compression screw according to claim 14 wherein the proximal end of said shaft that comprises the external proximal screw thread is the most proximal end of the compression screw.

20. A compression screw comprising:
a shaft having a longitudinal axis capable of being stretched, said shaft having a proximal end and a distal end, said proximal end of said shaft comprising an external proximal screw thread and said distal end of said shaft comprising a distal screw thread, wherein a pitch of said external proximal screw thread is finer than a pitch of said distal screw thread, said distal screw thread and said external proximal screw thread are spaced apart and separated by a portion of said shaft that is threadless, and said proximal end of said shaft comprises a drive feature for turning said shaft, wherein said compression screw is a single component, wherein said shaft is a single unitary piece of metal that is slotless,
wherein inserting said compression screw into bone across a fracture line is configured to generate a force, and wherein said force is configured to generate a stress in said shaft that causes said shaft to stretch to less than its elastic limit, wherein the shaft is configured to reversibly axially stretch along the longitudinal axis from an original un-stretched condition to a stretched condition, wherein the stretched condition is longer than the original un-stretched condition, and
wherein, after said shaft is inserted into the bone, said shaft is configured to attempt to axially contract along the longitudinal axis to the original un-stretched condition, thereby generating and maintaining compression across the fracture line.

21. The compression screw according to claim 20 wherein said external proximal screw thread and said distal thread have a cross sectional shape defined by an inclined portion and a flat portion, wherein the flat portion is substantially perpendicular to the longitudinal axis.

22. The compression screw according to claim 20 wherein the proximal end of said shaft that comprises the external proximal screw thread is the most proximal end of the compression screw.

\* \* \* \* \*